United States Patent [19]

Hermes

[11] Patent Number: 5,282,829
[45] Date of Patent: Feb. 1, 1994

[54] HOLLOW BODY IMPLANTS

[75] Inventor: Matthew E. Hermes, Easton, Conn.

[73] Assignee: United States Surgical Corporation, Norwalk, Conn.

[21] Appl. No.: 745,513

[22] Filed: Aug. 15, 1991

[51] Int. Cl.[5] ............................................. A61B 17/00
[52] U.S. Cl. .................................. 606/219; 606/220; 411/479
[58] Field of Search .............. 606/151, 153, 157, 158, 606/219, 220, 221; 422/423, 422; 411/457, 439, 487, 479

[56] References Cited

U.S. PATENT DOCUMENTS

| | | |
|---|---|---|
| 3,363,628 | 1/1968 | Wood .................................. 606/154 |
| 3,739,773 | 6/1973 | Schmitt et al. . |
| 3,918,455 | 11/1975 | Coplan ................................ 606/224 |
| 3,946,734 | 3/1976 | Dedrick et al. . |
| 3,991,766 | 11/1976 | Schmitt et al. ..................... 606/229 |
| 4,024,871 | 5/1977 | Stephenson . |
| 4,069,307 | 1/1978 | Higuchi et al. . |
| 4,144,317 | 3/1979 | Higuchi et al. . |
| 4,175,326 | 11/1979 | Goodson . |
| 4,351,337 | 9/1982 | Sidman . |
| 4,402,445 | 9/1983 | Green ................................... 227/19 |
| 4,434,796 | 3/1984 | Karapetian ......................... 606/220 |
| 4,513,746 | 4/1985 | Aranyi et al. ........................ 227/19 |
| 4,525,340 | 6/1985 | Lange et al. . |
| 4,673,565 | 6/1987 | Di Luccio et al. . |
| 4,696,300 | 9/1987 | Anderson ........................... 606/219 |
| 4,702,247 | 10/1987 | Blake, III et al. ................... 606/153 |
| 4,720,384 | 1/1988 | DiLuccio et al. . |
| 4,736,746 | 4/1988 | Anderson ........................... 606/219 |
| 4,743,448 | 5/1988 | Bahadir et al. . |
| 4,840,626 | 6/1989 | Linsky et al. . |
| 4,871,542 | 10/1989 | Vilhardt . |
| 4,961,931 | 10/1990 | Wong . |
| 4,976,715 | 12/1990 | Bay et al. ........................... 606/220 |
| 4,976,722 | 12/1990 | Failla .................................. 606/154 |
| 5,051,272 | 9/1991 | Hermes et al. ..................... 606/157 |
| 5,084,050 | 1/1992 | Draenert ............................. 606/77 |

FOREIGN PATENT DOCUMENTS 9014045 11/1990 European Pat. Off. ............ 606/224

Primary Examiner—Stephen C. Pellegrino
Assistant Examiner—Gary Jackson

[57] ABSTRACT

The present invention provides a surgical incision or wound closure implant device possessing an interior hollow core region while maintaining the mechanical beam characteristics of the overall structure. In the case of cored biodegradable implant devices the thickness of the cored region can be varied to regulate the speed at which the device is biodegraded. The core region may optionally be filled with a medicinal agent or a stabilizing material.

41 Claims, 7 Drawing Sheets

HOLLOW BODY IMPLANTS

BACKGROUND OF THE INVENTION

This invention relates to fastening devices, implants and articles used in surgical procedures.

Surgical fasteners such as staples, clips, clamps, bands, tacks, or other wound or incision closure devices are commonly used in surgical procedures to allow a surgeon to fasten, secure and/or repair body tissue quickly without the need for time consuming suturing. Examples of surgical fasteners are given in U.S. Pat. Nos. 4,994,073 or 4,950,284 or 4,934,364, or 4,932,960.

Surgical fasteners are designed to be inserted into and to join tissue or layers of tissue. In so doing, they are adapted to receive a mechanical load or stress without substantial deformation or breakage. The stress may be generated at different points in time and may arise from different stimuli. For example, when the fastener is a two-part device, such as that shown in U.S. Pat. No. 4,932,960, a generally U-shaped fastener member is ejected from a stapling device, passed through tissue, and lodged into a retainer member. Consequently, the backspan of the U-shaped fastener member receives a load when the pusher of the stapling device contacts the backspan and propels the fastener out of the device. The fastener member also receives loads when its prongs penetrate the tissue, and further, when the prongs contact and mate with the retainer. In order to function properly, the fastener and retainer should be designed and constructed to withstand operational stress without substantial deformation or breakage. Once in place, the fastener must also withstand the shearing stress placed upon the tissue, and consequently, on the fastener itself, which is created by the characteristics of tissue interaction in a living creature.

The ability of a fastener to withstand stress is determined by the kind of material, the amount of material, and the shape of the fastener's various structural members. It is desirable to optimize these variables, generally by providing the greatest strength to mass of material ratio so as to minimize the amount of foreign material in the body.

The structural members of surgical fasteners commonly have a solid circular, ellipsoidal, rectangular or polygonal aspect. The flex and bend strengths of such members are usually more than sufficient to withstand the loads required in surgical applications, e.g., firing the parts into tissue or during the holding period during which healing occurs and tissue strength is increasing.

Surgical fastening devices may be designed with open grooves or channels to guide the fastener component of a two-piece surgical fastening device from the stapler into a retainer component, see, for example U.S. Pat. No. 4,513,746. The retainer component receives the legs of the fastener component through tubular columns that become substantially completely filled by the legs of the fastener component. Other exteriorly disposed open grooves pertaining to surgical hemostatic clips are disclosed in U.S. Pat. Nos. 4,976,722 or 4,702,247. Such exterior grooves are designed to help grab and secure a blood vessel or artery. U.S. Pat. No. 3,918,455 discloses a hollow filament suture designed to receive and secure the shank of a suture needle. The hollow core of the suture is designed to collapse under stress. The collapsable nature of the core improves knotability through compressibility of the hollow filament under the tension of knotting.

Various materials are used in the manufacture of surgical fasteners and implants. These materials must be biocompatible, i.e., they do not adversely affect the surrounding living environment, and conversely, their performance is not adversely affected by the surrounding living environment. The materials may be inert non-absorbable or biodegradable. Inert materials may be fairly indestructible and maintain their form and function for extended periods of time.

Biodegradable materials are intended to break down and dissolve during and after the healing process. Biodegradation may occur, e.g., by hydrolysis as in the case of certain ester compounds or by enzymatic degradation as in the case of certain proteins. The time it takes for biodegradable fasteners to dissolve depends, inter alia, upon the inherent solubility of the material, the amount of the material present, the density of the material, and the amount of contact with bodily fluids that decompose the material. Optimally, a biodegradable fastener maintains its structural integrity in situ long enough for the tissue being fastened to gain sufficient strength to be self-supporting.

In general, a well-designed surgical fastener or implant should minimize the amount of material needed to create optimum structural integrity. Non-efficient use of materials wastes expensive resources and results in implants or fasteners that are heavier than necessary. Creating lighter implants or fasteners is desirable because less stress would be placed on the surrounding tissue system than might normally result from fasteners of excess mass. Moreover, in the case of biodegradable materials, the ability to exert greater control over adjustments in the density and amount of material used would permit greater regulation of the time it takes for the implant or fastener to be dissolved and absorbed into the living system. Indeed, once the fastened tissue is capable of suitable self-support, it is advantageous for the biodegradable material to be dissolved as quickly as possible to reduce continuing tissue interaction with the material.

Consequently, the need to optimize the strength to mass ratio of surgical implants and fasteners is clear. The present invention optimizes the mass to strength ratio in the creation of structurally sound surgical implants and fasteners.

OBJECTS AND SUMMARY OF THE INVENTION

Accordingly, it is an object of the invention to maximize the strength of surgical implants while using a minimum amount of material.

It is another object of the invention to provide a light-weight surgical implant.

It is yet another object of the invention to provide biodegradable surgical implants whose decomposition is regulated to suit particular applications.

It is as further object of the invention to provide a focal drug delivery device.

It is still another object of the invention to provide a stable surgical implant.

Other objects and advantages of this invention will become apparent from the following summary and detailed description of the invention.

A surgical implant according to the present invention possesses a core occupying an interior region of the device. The cored implant maintains its form and function due to the ability of the structural members surrounding the cored region to function with the mechanical characteristics of a beam. The implant may be formed into a surgical connector, clip, clamp, band or other fastener device that can function to close incisions or wounds or may otherwise be made to contact and exert or receive pressure or stress within a living system.

The cored region of the implant may be continuous or it may be divided into sections throughout the implant. In certain cases the core may extend through the implant and end as an aperture on the implant. In other cases, the core is a sealed region within the implant. The implant may be made from an inert non-absorbable material or from a biodegradable material. The core region of the implant may optionally be filled with a stabilizing material or with a medicinal agent.

DETAILED DESCRIPTION OF THE INVENTION

Figure 1:
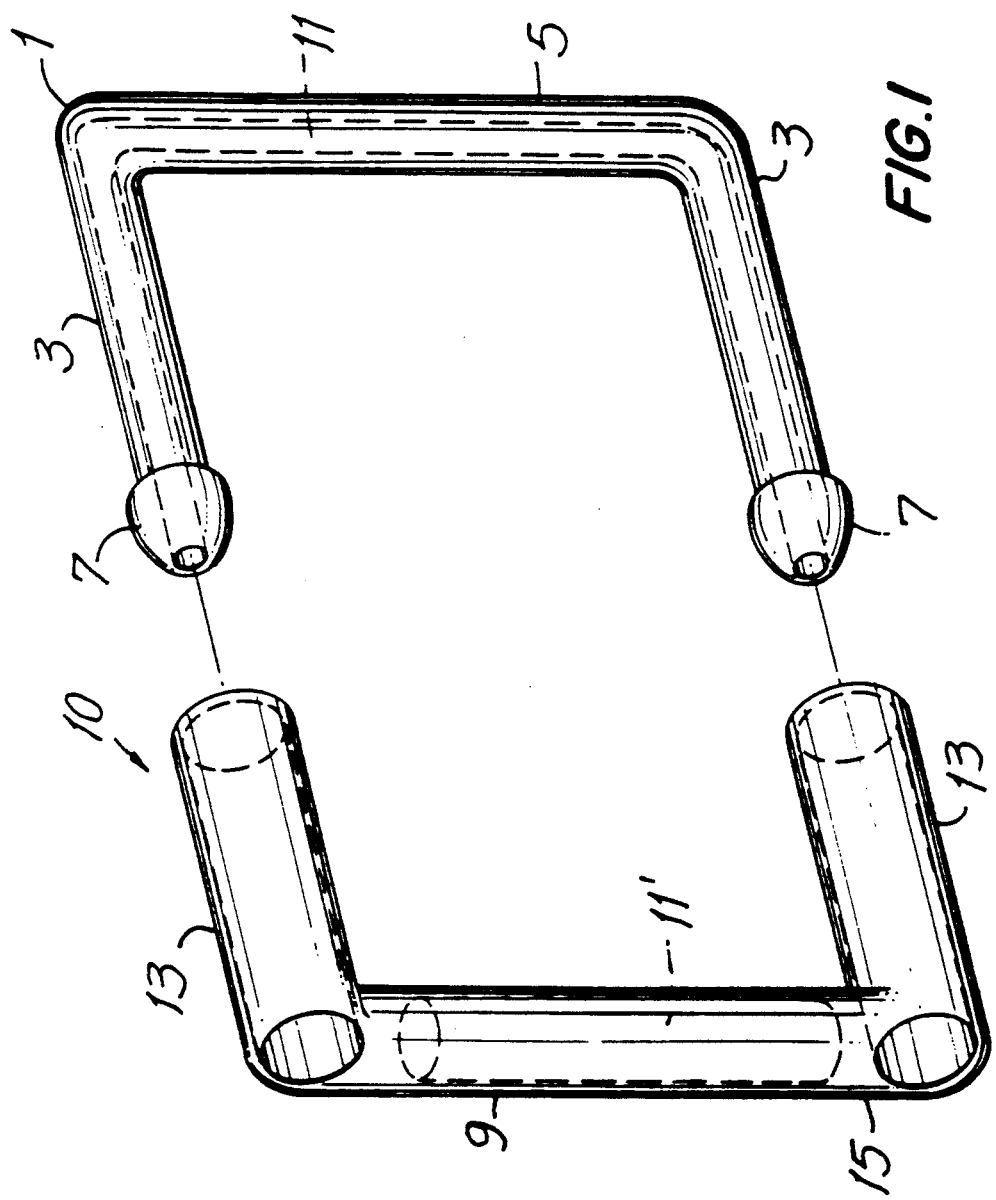
FIG. 1 is a perspective view of an implant device in the nature of a surgical fastener in accordance with the present invention, further depicting a cored region in phantom.

The implant device illustrated in FIG. 1 is a surgical fastener 10 constructed in accordance with the present invention. A U-shaped fastener member 1 has two prongs 3 attached to one another via a backspan 5. The prongs 3 have barbs 7 at their ends which mate and engage a retainer member 9. A novel core 11 runs the entire length of the fastener member 1 and the beam-like characteristics of the overall structure are maintained. As used herein, the "core" or "cored region" is an interiorly disposed hollow section which may be completely enclosed, or open at one or more locations on the surface of the implant. As such, the fastener member 1 is capable of carrying concentrated as well as evenly distributed load forces. The load forces normally act transverse to the longitudinal axis of the core. At any point along the fastener member 1 the shear force and bending moment acting on the beam cross section is used to balance the external loads on either side of the cross section.

When a load is applied to the fastener, such as when the fastener member 1 is propelled from a stapler into tissue, a pusher from the stapler contacts the backspan 5 and forces the fastener member 1 out of the stapler. The stress from the contact is generally evenly distributed over the backspan 5 and the rest of the fastener member 1. Notwithstanding the cored region, the fastener member 1 acts in a manner mechanically similar to, or better than, the backspan of a fastener not possessing a cored region.

When the fastener member 1 pierces the tissue to be fastened, the barbs 7 initially receive most of the force of entry and transmit the force and consequent stress to the rest of the fastener member 1. As above, the fastener member 1 and its core region 11 have the mechanical characteristics of a beam and concentrated forces are distributed over the fastener member 1. External forces to which the fastener member 1 is subjected are balanced over the cross section of the beam and the cored fastener member 1 performs in a manner mechanically similar to, or better than, fasteners not possessing such a core.

The retainer member 9 has two tubular columns 13 which are adapted to receive and engage the barbs 7 and a portion of prongs 3 of the fastener member 1. The columns 13 are connected via a bridge 15 containing a hollow cored region 11'. The retainer 9 functions in much the same mechanical manner as a retainer that does not have the cored region 11'. The hollow cored regions 11 and 11' facilitate construction of a structurally sound implant device with less material than a similar solid device. In mass production, the present invention allows a substantial economic savings with consequent conservation of resources and reduces the amount of foreign material introduced to the body. Moreover, the hollow nature of the core region permits instillation of various substances which are capable of performing diverse functions.

In one embodiment, the hollow cored region is filled with a medicament or medicinal agent, generally in a pharmaceutically acceptable vehicle. For convenience, the hollow cored region is described as containing a medicinal, but the term "medicinal" is used in its broadest sense and includes any substance or mixture of substances which may have any clinical use. Thus, it is understood that the hollow core may contain a drug, enzyme, peptide or diagnostic agent such as a releasable dye which may have no biological activity per se. Instillation of a medicinal into a surgical wound or incision closure device permits focal application of drug therapy once the device is in place. Focal application can be more desirable than general systemic application in some cases, e.g., chemotherapy for localized tumors, because it produces fewer side effects in distant tissues or organs and also concentrates therapy at intended sites. Focal application of growth factors by a wound or incision closure device is an ideal drug delivery system to speed healing of the wound or incision.

The material which makes up the implant may be porous, and depending on the size of the pores, will allow the medicinal to diffuse out of the cored region at a controlled rate. Methods by which the number and size of pores disposed within polymeric materials may be controlled are well-known to those with skill in the art. When the core is filled with a medicinal, e.g., in a pharmaceutically acceptable fluid vehicle, and the device is placed in tissue, the medicinal penetrates the walls of the device and diffuses into the surrounding environment. The rate of diffusion is determined by the size and number of the pores and is governed by first order kinetics, i.e., the rate of diffusion is directly proportional to the concentration of medicinal. In another embodiment, osmotically active particles are placed in the cored region along with the medicinal and its fluid vehicle. When placed in an aqueous medium, the osmotically active particles imbibe or absorb water and expand, thereby pressing the medicinal out from the cored region and into the surrounding environment. The rate of diffusion in this case is relatively constant, i.e., governed by zero order kinetics.

Figure 2:
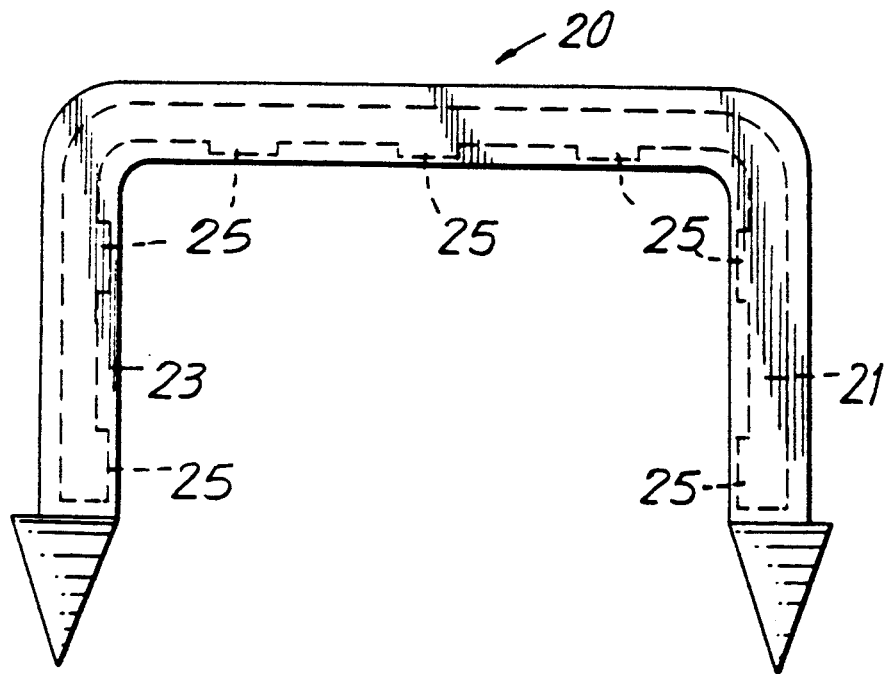
FIG. 2 is a perspective view of an implant device in the nature of a surgical fastener in accordance with the present invention, further depicting a crenelated cored region in phantom.

In addition to delivery of a medicinal by diffusion through pores disposed in the walls of the implant device, delivery can also be effected when the biodegradable material surrounding the core degrades and disappears. When a biodegradable wall or a portion thereof is degraded, perforations in the wall are formed which allow the medicinal contained in the core to diffuse or leak from the perforations. This characteristic of the invention can be used to great advantage, i.e., the thickness of the walls can be varied to ultimately control the rate of release of the medicinal. FIG. 2 illustrates a biodegradable U-shaped surgical fastener 20 having a crenelated core region 21 substantially extending through the entire length of the fastener 20. The wall 23 surrounding the core 21 is crenelated to provide relatively thin portions 25 that, when contacted with bodily tissue, degrade faster than the other thicker parts of the fastener 20. The medicinal is delivered to target areas when the thin portions 25 degrade and perforations are formed which act as conduits for the medicinal. The thin portions 25 are provided toward the interior radius of the fastener 25 to "point" the conduits and, consequently, the medicinal toward the tissue being fastened and treated. It should be understood that conduits can be provided to "point" in any desired direction. As above, the core region 21 within the fastener 20 helps maintain the fastener's beam-like attributes.

Figure 3:
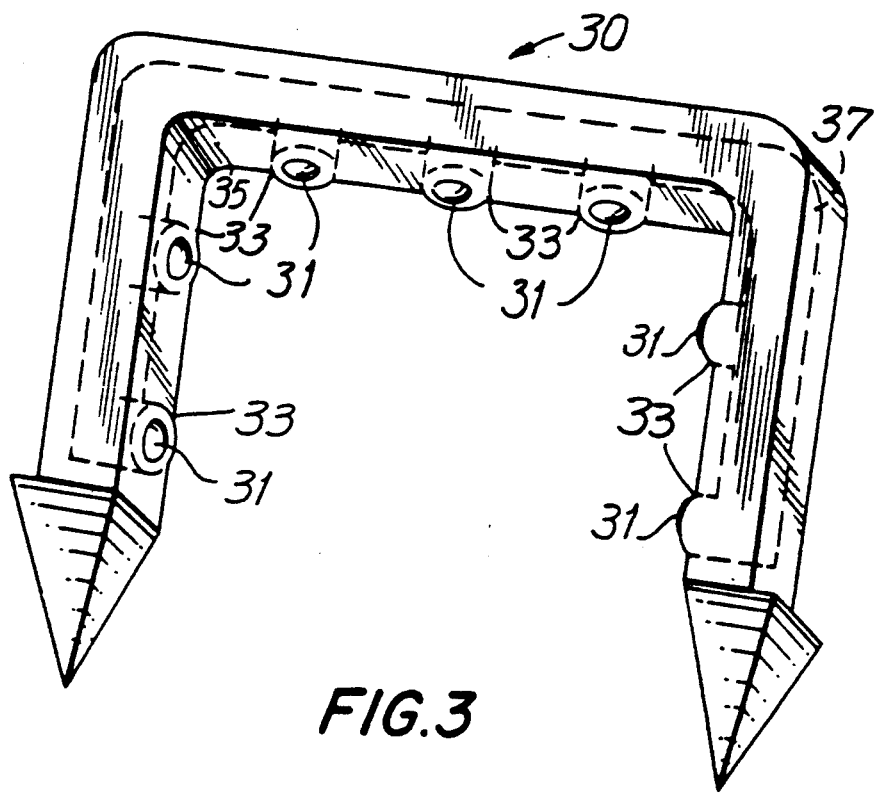
FIG. 3 is a perspective view of an implant device in the nature of a surgical fastener in accordance with the present invention further depicting a crenelated cored region in phantom wherein apertures leading to the cored region are covered by plugs.

Referring now to FIG. 3, and in another aspect of the invention, a surgical fastener 30 made of inert material is fitted with biodegradable plugs 31 that fit into corresponding apertures 33 in the wall 35 of the fastener 30. As above, a hollow crenelated core 37 is filled with a medicinal. When the fastener 30 is applied to bodily tissue, the plugs 31 degrade and eventually disappear and the medicinal diffuses or leaks from the fastener 30 to the target area.

When the implant is constructed of a relatively inert material such as titanium, titanium alloy, chromium-cobalt-molybdenum alloy, stainless steel, polypropylene, or other polymers, the vehicle used for the medicinal can be aqueous. If the material used is a biodegradable or bioresorbable material, such as polyglyolic acid, polylactic acid, copolymer blends of polyglycolic acid and polylactic acid, caprolactone, reconstituted collagen, polymers of p-dioxanone, polyesters, polyamino acids such as casein, albumen and the like, polyhydric alcohol polymers such as polyvinyl alcohol, trimethylene carbonate and others, a suitable medicinal and medicinial vehicle would optimally have little or no effect on the integrity of the device, i.e., the medicinal and/or the vehicle would not degrade the device.

Examples of classes of medicinals that can be used in accordance with the present invention are antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunosuppressants, gastrointestinal drugs, diuretics, steroids and enzymes. It is also intended that combinations of medicinals can be used in accordance with the present invention.

The cored region of a biodegradable implant can also be filled with a stabilizing material such as glycerol, calcium lactate in glycerol, or certain cellulose derivatives. Stabilizing fluids are useful in prolonging the storage capability of biodegradable implants.

A further advantage of biodegradable cored implants according to the present invention is that they have less mass then similarly sized solid implants but have approximately the same or better capacity to bear a mechanical load. Consequently, the implant device can hold together any tissue that an equivalent solid device would, but can be degraded at a much faster rate because of 1) the increased surface area available for contact with biodegrading fluids and 2) the smaller amount material that needs to be biodegraded. Thus, a device in accordance with the present invention can be designed to remain in contact with the tissue for a shorter period of time than a solid implant and is thus less likely to cause contact related tissue reaction. The thickness of the walls surrounding the cored region can be varied to regulate the speed at which decomposition occurs, i.e., the thicker the wall, the longer to decompose.

Figure 4:
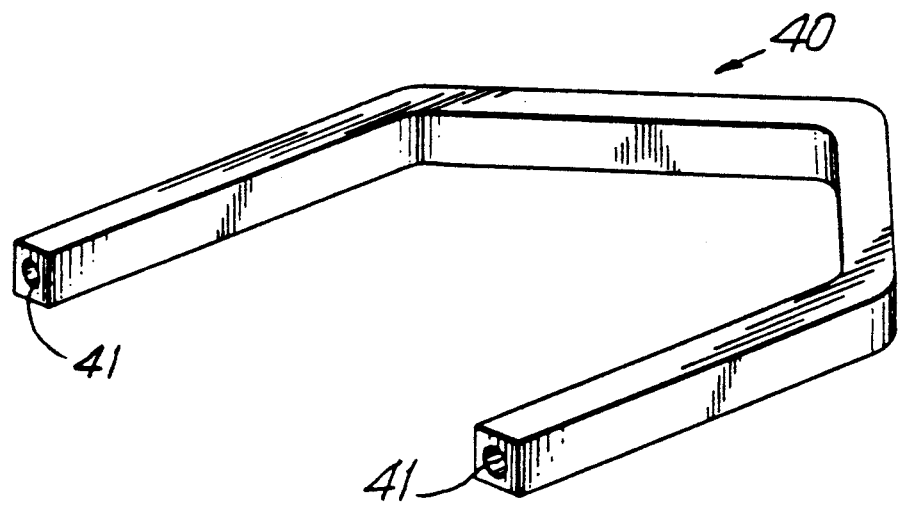
FIG. 4 is a perspective view of an implant device in the nature of a surgical clip in accordance with the present invention wherein the cored region ends as apertures.
Figure 5:
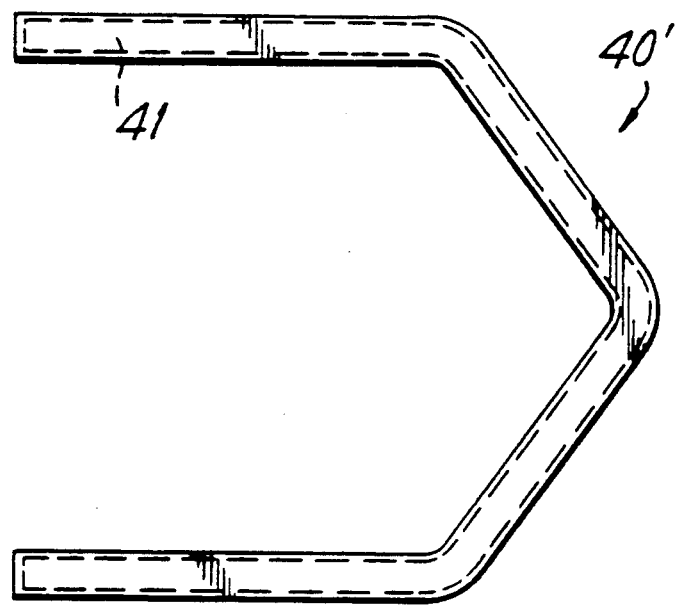
FIG. 5 is a top view of an implant device in the nature of a surgical clip in accordance with the present invention wherein the cored region is shown in phantom and the cored region is sealed at both ends of the clip.

Referring now to FIG. 4, a U-shaped surgical clip 40 according to the instant invention is illustrated. Ordinarily, during a surgical procedure, the clip 40 is formed around a vein, artery or duct so that legs of the clip 40 assume a substantially parallel orientation and fluid flow in the vein, artery or duct is cut off. A hollow core 41 extends continuously throughout the clip 40 and can remain open at the ends as in FIG. 4. Alternatively, the ends can be sealed, as is shown in FIG. 5. In FIG. 5, the core 41' is shown as phantom lines. In either case, the core region within the clip provides the basis for beam-like attributes. As above, the core region can be filled with a medicinal or a stabilizing agent to similar advantage.

Figure 6A:
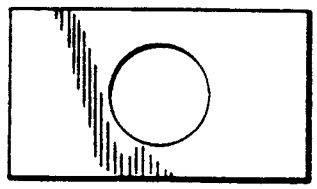
FIGS. 6A-6H are cross sectional views illustrating various core configurations in accordance with the invention.
Figure 6B:
Figure 6C:
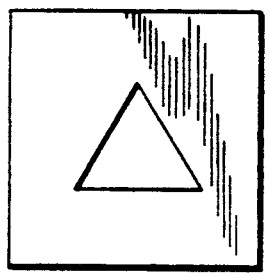
Figure 6D:
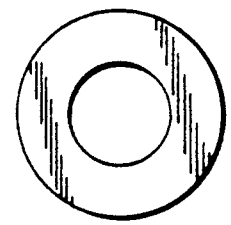
Figure 6E:
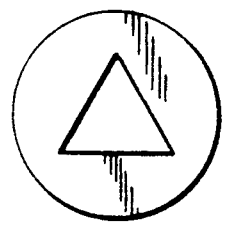
Figure 6F:
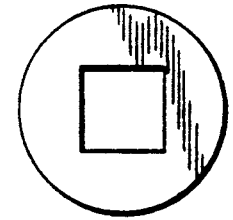
Figure 6G:
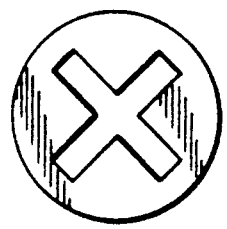
Figure 6H:
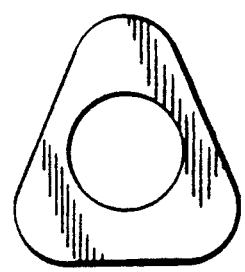

In general, the core region can have a variety of shapes independent of the shape of the implant device itself. The core can have a circular cross section within a rectangular shaped device member as shown in FIG. 6A or the core can have a rectangular cross section within a rectangular shaped device member as shown in FIG. 6B. FIGS. 6C-6H are other illustrative examples of various cross-sectional embodiments according to the present invention. This invention applies to cored implants generally and it is contemplated that any shaped core may be located in any surgical fastening device and still be within the scope of the appended claims.

Figure 7:
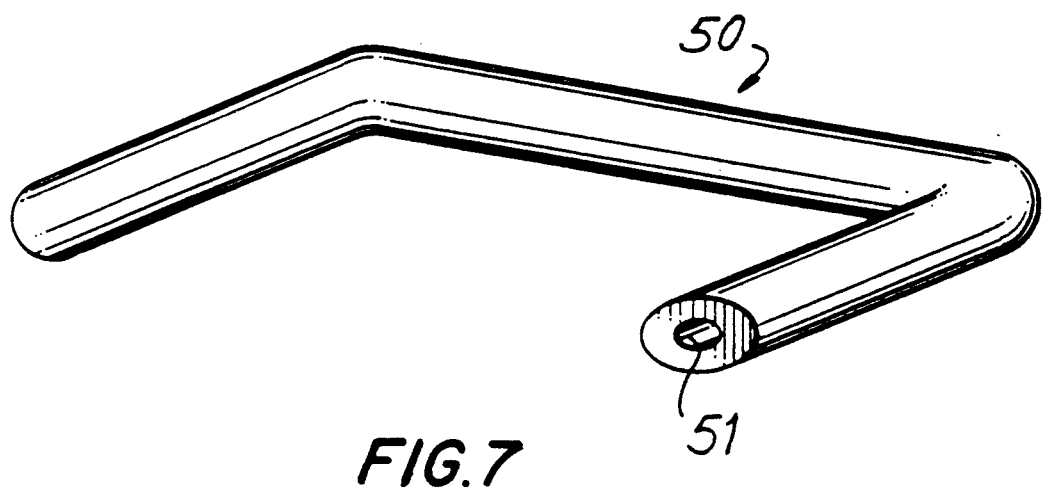
FIG. 7 is a perspective view of an implant device in accordance with the invention, illustrating a core of cylindrical cross-section located in an ellipsoidally configured surgical staple.
Figure 8:
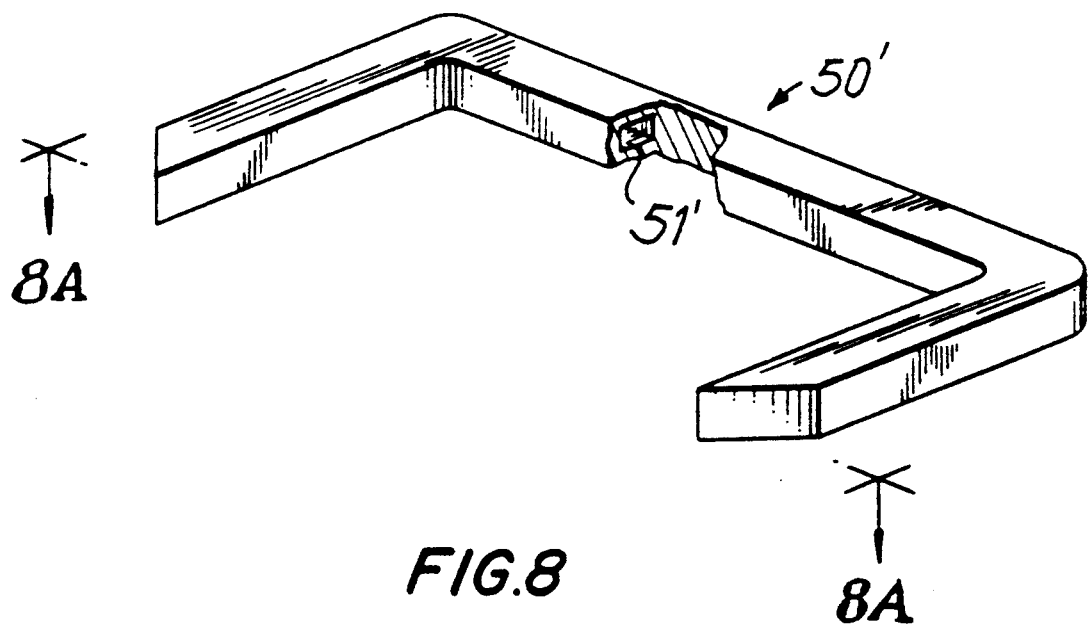
FIG. 8 is a partial cut-away perspective view of an implant device in accordance with the invention, illustrating a core of rectangular cross-section located in a rectangularly configured surgical staple.
Figure 8A:
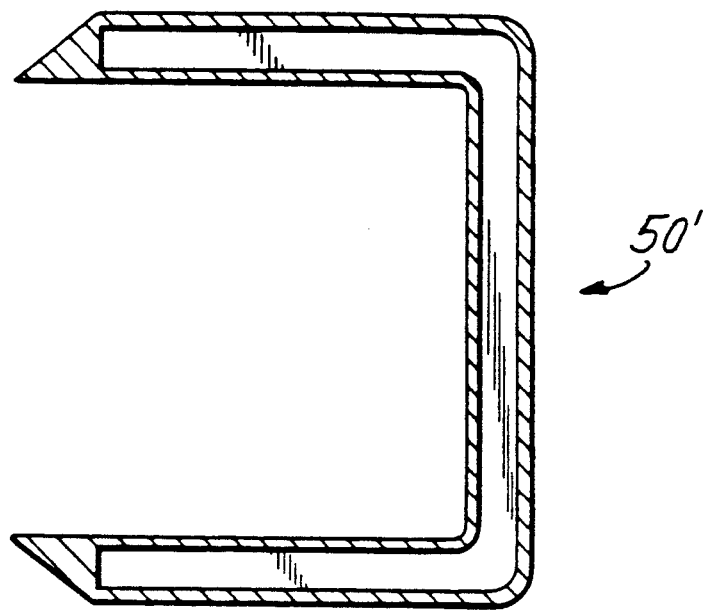
FIG. 8A is a cross sectional plan view of the surgical staple illustrated in FIG. 8.

The present invention is also applicable to surgical staples, examples of which are illustrated in FIGS. 7 and 8. In FIG. 7, a surgical staple 50 is generally U-shaped and has an elliptical cross-section. The core region 31 has a circular cross-section and extends the entire length of the staple 50. It is noted that any shape core (see, e.g., FIGS. 6A-6H) would be suitable as long as the desired strength is imparted to the overall device. The staple 50' may also have a rectangular aspect as is shown in FIG. 8. Also shown is a rectangular core 51'. FIG. 8A depicts the staple 50' in cross-section, further depicting the rectangular core 51' stretching nearly the entire length of the staple 50'. Staples constructed in accordance with the instant invention have approximately the same or better mechanical load bearing characteristics than staples without a core region. The core region, 51 or 51' may be open or sealed at the ends.

Figure 9:
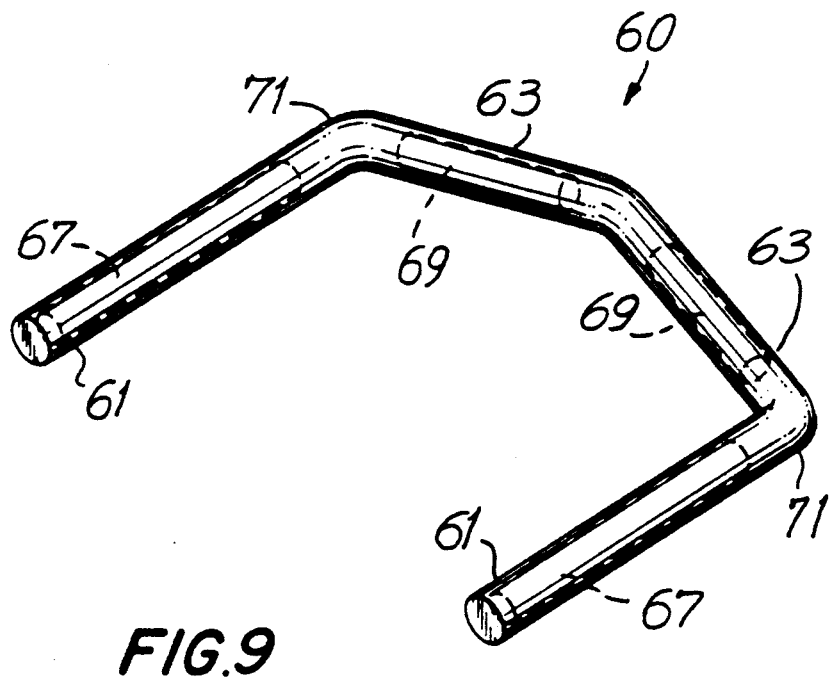
FIG. 9 is a perspective view of an implant device in the nature of a surgical clip in accordance with the invention, further illustrating, in phantom, a multiplicity of cored regions separated by solid regions.

In some instances, it may be desirable to provide a series of discontinuous core regions within an implant device. An example of such a device is shown in FIG. 9. A generally U-shaped surgical clip 60 has arms 61 extending outwardly from a crown 63. The apex 65 of the crown 63 is a juncture at which the clip 60 is bent. The core regions 67 of the arm of the clip 60 are separated from the core regions 69 of the crown by solid sections 71 which are located at bending points. The apex 65 region is a solid section separating the core regions 69 of the crown 63. The solid sections may be used to impart increased resilience or resistance at strategic junctures. In other cases, the solid regions may be positioned at various places along the arms 67 of crown 63. In any event, the solid regions may be placed in strategic positions between the cored regions of any implant device in accordance with the present invention.

Figure 10:
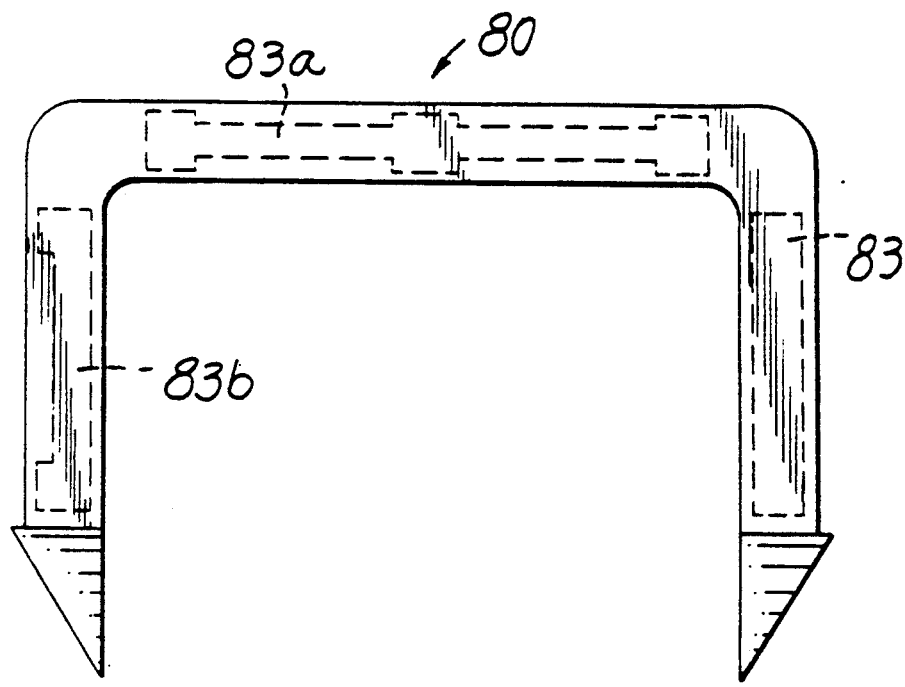
FIG. 10 is a perspective view of an implant device in the nature of a surgical fastener in accordance with the present invention further depicting a plurality of crenelated cored regions in phantom.

The existence of multiple core regions or compartments is useful in certain aspects of the invention relating to delivery of medicinals. The biodegradable U-shaped surgical fastener 80 illustrated in FIG. 10 is composed of three separate hollow core regions or compartments 83, 83a and 83b. Each compartment can be filled with a different medicinal agent or combination of medicinal agents. In this manner, medicinals that may be incompatible with each other are kept separate but are still delivered to target sites. Incompatibility may result from, e.g., different solubilities of different medicinals in a vehicle or inactivity of the medicinals due to complex formation, etc. The compartments can be constructed to release their contents at different points in time. Thus, compartment 83 is not crenelated and will take longer to release medicinals than crenelated compartments 83a and 83b.

Figure 11:
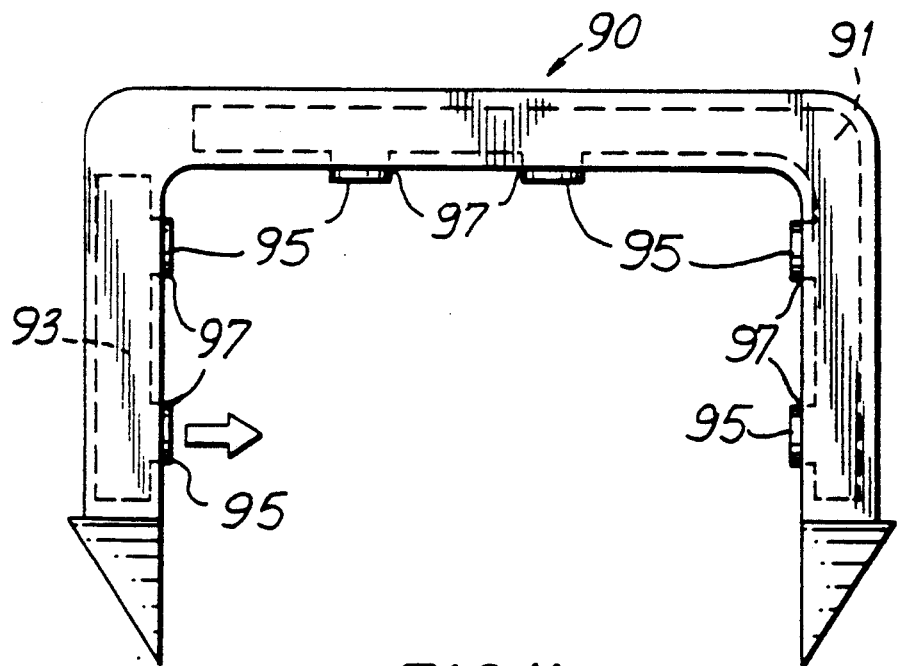
FIG. 11 is a perspective view of an implant device in the nature of a surgical fastener in accordance with the present invention further depicting a plurality of crenelated cored regions in phantom wherein apertures leading to the cored regions are covered by plugs.

Similarly, in FIG. 11, an inert or biodegradable U-shaped fastener 90 is composed of two separate compartments 91 and 93 which can be used to separate incompatible medicinals. Biodegradable plugs 95 fit into corresponding holes 97 in the compartments 91 and 93 to prevent any medicinal contained therein from diffusing or leaking out until the fastener 90 is contacted with bodily tissues. When the plugs 95 degrade, the medicinal diffuses or leaks out to the target site. The speed of release of medicinal from compartment 91 can be regulated relative to compartment 93 by varying the thickness of the plugs 95. For example, if the plugs 95 sealing compartment 93 are made thicker than those sealing compartment 91, they will take longer to degrade and, consequently, the medicinal will be released from compartment 91 first. Alternatively, the plugs 95 can be made of different biodegradable materials which have different rates of decomposition. In this way, plugs having slower rates of decomposition than other plugs maintain a sealed compartment longer than the other plugs covering other compartments, thus causing different rates of medicament delivery and permitting sequential medicament release.

The principles, preferred embodiments and modes of operation of the invention have been described in the foregoing specification. The invention which is intended to be protected herein, however, is not to be construed as limited to the particular forms disclosed, since they are to be regarded as illustrative rather than restrictive. Variations and changes may be made by those skilled in this art without departing from the spirit of the present invention.

What is claimed is:

1. A surgical implant possessing a core contained entirely within an interior region of the implant, the implant comprising tissue piercing means, the implant being thereby independently insertable and configured to receive and support a mechanical load in use.

2. A surgical implant device according to claim 1 comprising a wound closure device.

3. A surgical implant according to claim 2, wherein the wound closure device is a surgical connector, clip, clamp, staple, tack, or band.

4. A surgical implant according to claim 1 wherein the core occupies a portion of the surgical implant, other portions having a solid cross-section.

5. A surgical implant according to claim 4 wherein at least one core region abuts at least one solid region.

6. A surgical implant according to claim 1 wherein the core extends from the interior region to at least one non-coaxially aligned exterior aperture.

7. A surgical implant according to claim 6, further comprising at least one biodegradable plug which is capable of mating with and sealing the at least one aperture.

8. A surgical implant according to claim 7 further comprising at least first and second biodegradable plugs, wherein said first biodegradable plug is adapted to biodegrade at a different rate compared to said second biodegradable plug.

9. A surgical implant according to claim 1 wherein the implant is fabricated from a biodegradable material.

10. A surgical implant according to claim 9 wherein the biodegradable material is selected from the group consisting of lactide, glycolide, caprolactone, dioxanone and trimethylene carbonate.

11. A biodegradable surgical implant possessing a core contained entirely within an interior region of the implant, the implant comprising tissue piercing means, the implant being adapted to receive and support a mechanical load in use wherein the core is crenelated.

12. A surgical implant possessing a core contained entirely within an interior region of the implant, the implant comprising tissue piercing means, the implant being adapted to receive and support a mechanical load in use wherein the implant is fabricated from a material selected from the group consisting of chromium-cobalt-molybdenum alloy, titanium, stainless steel and titanium alloy.

13. A surgical implant possessing a core contained entirely within an interior region of the implant, the implant comprising tissue piercing means, the implant being adapted to receive and support a mechanical load in use wherein the core of the implant contains at least one medicinal.

14. A surgical implant according to claim 13 wherein the medicinal is selected from the group consisting of antimicrobials, analgesics, antipyretics, anesthetics, antiepileptics, antihistamines, anti-inflammatories, cardiovascular drugs, diagnostic agents, sympathomimetics, cholinomimetics, anti-muscarinics, antispasmodics, hormones, growth factors, muscle relaxants, adrenergic neuron blockers, anti-neoplastics, immunosuppressants, gastrointestinal drugs, diuretics, steroids and enzymes.

15. A surgical implant according to claim 13 further comprising at least first and second core regions, wherein at least one medicinal is instilled into each of said at least first and second core regions, the first said core region adapted to release its contents at a different rate compared to said second core region.

16. A surgical implant according to claim 13 wherein the cored region of the implant contains osmotically active particles.

17. A surgical implant possessing a core contained entirely within an interior region of the implant, the implant comprising tissue piercing means, the implant being adapted to receive and support a mechanical load in use wherein the core contains a stabilizing fluid.

18. A surgical implant according to claim 17 wherein the stabilizing fluid is selected from the group consisting of glycerol and glycerol plus calcium lactate.

19. A surgical implant selected from the group consisting of connectors, clips, clamps, tacks, bands, and fasteners comprising a core contained entirely within an interior region of said implant, said implant containing tissue piercing means, said implant being thereby independently insertable and configured to receive and support a mechanical load in use.

20. A surgical implant selected from the group consisting of connectors, clips, clamps, tacks, bands, staples and fasteners comprising structural members having at least one hollow compartment entirely disposed therein, the structural members being configured to receive and support a mechanical load in use, the implant further comprising tissue piercing means, the implant being independently insertable.

21. A surgical implant according to claim 20 wherein the implant is fabricated from a biodegradable material.

22. A surgical implant selected from the group consisting of connectors, clips, clamps, staples, tacks, bands and fasteners comprising structural members having at least one hollow compartment disposed therein, the structural members being adapted to receive and support a mechanical load in use wherein the hollow compartment of the implant contains at least one medicinal.

23. A surgical implant selected from the group consisting of connectors, clips, clamps, staples, tacks, bands and fasteners comprising structural members having at least one hollow compartment disposed therein, the structural members being adapted to receive and support a mechanical load in use wherein the hollow compartment contains a stabilizing fluid.

24. A method of controlling the rate of decomposition of an independently insertable biodegradable surgical implant having tissue piercing means comprising: forming a hollow core region contained entirely within the implant and contacting the implant with a suitable degradation medium.

25. A method of controlling the rate of decomposition of a biodegradable surgical implant selected from the group consisting of connectors, clips, clamps, staples, tacks, bands and fasteners comprising: forming a hollow core region completely within the implant and contacting the implant with a suitable degradation medium and delivering medicinals by instilling a medicinal into the hollow core region.

26. A surgical implant selected from the group consisting of staples and clips, the implant comprising a first leg connected to a second leg by a backspan, the backspan comprising at least one interiorly disposed hollow core.

27. A surgical staple according to claim 26 further comprising at least one interiorly disposed hollow core disposed at least within the first leg.

28. A surgical staple according to claim 27, further comprising at least one substance selected from the group consisting of medicinals and stabilizing fluids disposed within the at least one interiorly disposed hollow core.

29. A surgical implant according to claim 27 further comprising at least one non-coaxially disposed aperture which connects the at least one hollow core to the exterior of the implant.

30. A surgical implant according to claim 29 further comprising at least one biodegradable plug adapted to seal said at least one aperture.

31. A surgical implant according to claim 27 wherein said hollow core disposed at least within the first leg extends to and communicates with said interiorly disposed hollow core of said backspan.

32. A surgical implant according to claim 26, further comprising at least one substance selected from the group consisting of medicinals and stabilizing fluids disposed within the at least one interiorly disposed hollow core.

33. A surgical implant according to claim 26 further comprising at least one aperture disposed in the backspan which aperture connect the at least one hollow core to the exterior of the implant.

34. A surgical implant according to claim 33 further comprising at least one biodegradable plug adapted to seal said at least one aperture.

35. A surgical tack comprising a shaft having at least one hollow core disposed completely within the shaft.

36. A surgical tack according to claim 35 further comprising a substance selected from the group consisting of medicinals and stabilizing fluids disposed within the at least one hollow core.

37. A surgical tack according to claim 35 further comprising at least one aperture disposed non-coaxially in relation to the shaft which aperture connect the at least one hollow core with the exterior of the tack.

38. A surgical implant according to claim 33 further comprising at least one biodegradable plug adapted to seal said at least one aperture.

39. A surgical fastener comprising a U-shaped member, the U-shaped member having two prongs, each prong attached to a backspan, said backspan comprised of at least one interiorly disposed hollow core, the fastener further comprising a retainer member which engages said prongs of said U-shaped member.

40. A surgical fastener according to claim 39 wherein at least one of said shafts comprise at least one interiorly disposed hollow core.

41. A surgical fastener according to claim 39 wherein said retainer member comprises at least one interiorly disposed hollow core.

* * * * *